United States Patent [19]

Heitkämper et al.

[11] 4,430,505
[45] Feb. 7, 1984

[54] PROCESS FOR THE PREPARATION OF N,O-DISUBSTITUTED URETHANES USEFUL FOR THE PREPARATION OF ISOCYANATES

[75] Inventors: Peter Heitkämper, Dormagen; Klaus König, Leverkusen; Kurt Findeisen, Odenthal; Rudolf Fauss, Cologne; Rudolf Sundermann, Leverkusen, all of Fed. Rep. of Germany

[73] Assignee: Bayer Aktiengesellschaft, Leverkusen, Fed. Rep. of Germany

[21] Appl. No.: 197,032

[22] Filed: Oct. 15, 1980

[30] Foreign Application Priority Data

Oct. 27, 1979 [DE] Fed. Rep. of Germany ....... 2943551

[51] Int. Cl.$^3$ ............... C07C 125/065; C07C 125/073
[52] U.S. Cl. .................................. 560/24; 260/465.4; 260/465 D; 260/404; 260/239 E; 260/938; 560/22; 560/25; 560/27; 560/28; 560/29; 560/30; 560/31; 560/32; 560/115; 560/145; 560/157; 560/158; 560/160; 560/161; 544/164; 544/322; 546/312; 546/334; 549/28; 549/467
[58] Field of Search ............... 260/465.4, 465 D, 404, 260/239 E, 938, 346.71; 560/22, 24, 25, 27, 28, 30, 29, 31, 32, 115, 145, 157, 158, 160, 161; 544/164, 322; 546/312, 334; 549/28; 548/378

[56] References Cited

U.S. PATENT DOCUMENTS

| 2,409,712 | 10/1946 | Schweitzer | 260/453 A |
| 2,806,051 | 9/1957 | Brockway | 560/24 |
| 3,627,813 | 12/1971 | Abbate et al. | 560/25 |
| 4,178,455 | 12/1979 | Hirai et al. | 560/24 |
| 4,388,238 | 6/1983 | Heitkämper et al. | 560/22 X |

OTHER PUBLICATIONS

Adams et al., Chemical Reviews (1965) vol. 65, 567–572.

Primary Examiner—Bernard Helfin
Attorney, Agent, or Firm—Gene Harsh; Joseph C. Gil; Lyndanne M. Whalen

[57] ABSTRACT

A process for the preparation of N,O-disubstituted urethanes. Urea or polyurets, primary amines and alcohols are reacted at 120°–350° C. in the presence of N-substituted urethanes and/or N-mono- or N,N'-disubstituted ureas or polyureas. In a preferred embodiment, the reactants further include catalysts known to be useful in esterification of carboxylic acids. The urethanes produced in accordance with this process are particularly useful as starting materials for preparation of isocyanates.

15 Claims, No Drawings

PROCESS FOR THE PREPARATION OF N,O-DISUBSTITUTED URETHANES USEFUL FOR THE PREPARATION OF ISOCYANATES

BACKGROUND OF THE INVENTION

This invention relates to an improved process for the preparation of urethanes in which urea or polyurets, amines and alcohols are reacted in the presence of N-unsubstituted urethanes and/or N-mono- or N,N'-disubstituted ureas or polyureas.

It is known that urethanes may be formed by reacting organic isocyanates with alcohols. This reaction is reversible, i.e., the urethanes so formed may be thermally split into the isocyanate and the alcohol on which they are based (see, for example, U.S. Pat. No. 2,409,712). Urethanes which may be thermally split into isocyanates are, therefore, potential starting materials for the preparation of isocyanates.

Isocyanates have been almost universally prepared by reacting primary amines with phosgene. However, the preparation of urethanes without phosgene and the subsequent thermal splitting of these urethanes would be an interesting alternative. One method for preparing urethanes without the use of phosgene is to react urea with amines and alcohol. Such a method is described in U.S. Pat. Nos. 2,409,712 and 2,806,051. However, these known methods produce urethanes which contain numerous secondary products in inadequate yields.

SUMMARY OF THE INVENTION

It is an object of the present invention to provide an improved process for preparing urethanes by reacting urea with alcohols and amines in such a way that the N,O-disubstituted urethanes are obtained in amounts greater than those achieved with known methods.

It has now surprisingly been found that this object may be achieved by using materials containing carbonyl groups in addition to the urea and/or polyurets, amines and alcohols known in the art.

The present invention relates to a process for the preparation of N,O-disubstituted urethanes by reacting:
(a) urea or polyurets with
(b) primary amines and
(c) alcohols at temperatures of from 120° to 350° C., characterized in that
(d) N-unsubstituted urethanes and/or
(e) N-mono- or N,N'-disubstituted ureas or polyureas
are used as further reactants.

The process according to the present invention is particularly suitable for the preparation of urethanes corresponding to the following general formula:

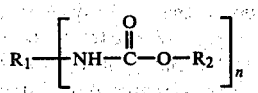

wherein
$R_1$ represents an optionally substituted aliphatic hydrocarbon radical containing from 1 to 18 carbon atoms, an optionally substituted cycloaliphatic hydrocarbon radical containing from 3 to 18 carbon atoms, an optionally substituted aromatic hydrocarbon radical containing from 6 to 15 carbon atoms, an optionally substituted araliphatic hydrocarbon radical containing from 7 to 14 carbon atoms or an optionally substituted 5- or 6-membered heterocyclic radical which, in addition, may be fused wth a benzene ring,
$R_2$ represents an optionally substituted alkyl radical containing from 1 to 20 carbon atoms, an optionally substituted cycloalkyl radical containing from 3 to 16 carbon atoms and an optionally substituted aralkyl radical containing from 7 to 14 carbon atoms, and
n represents an integer of from 1 to 3.
When n represents 2 or 3, at least 2 carbon atoms should be arranged between the 2 urethane groups attached to the radical $R_1$.

Substituents for the aliphatic or cycloaliphatic radicals $R_1$ and $R_2$ include $C_6$–$C_{10}$ aroxy, $C_1$–$C_6$ alkoxy, $C_1$–$C_6$ alkoxy-$C_2$–$C_4$ alkoxy, $C_1$–$C_6$ acyl, $C_1$–$C_6$ alkyl mercapto, $C_6$–$C_{10}$ aryl mercapto, $C_1$–$C_{12}$ alkyl carbonyl, bis-($C_1$–$C_8$ alkyl)-amino, $C_1$–$C_6$ acyl amino, nitro, cyano and thiocyano radicals.

In addition to these substituents, suitable substituents for the aromatic or araliphatic radicals $R_1$ and $R_2$ include $C_1$–$C_{12}$ alkyl, $C_1$–$C_{12}$ alkyl sulfonic acid ester and sulfonamide radicals.

The preferred products of the process of the present invention are those corresponding to the above-given general formula wherein
$R_1$ represents an aliphatic hydrocarbon radical containing from 3 to 18 carbon atoms, a cycloaliphatic hydrocarbon radical containing from 6 to 15 carbon atoms or an optionally methyl-, methoxy- or chlorine-substituted $C_6$–$C_{15}$ hydrocarbon radical optionally containing methylene bridges,
$R_2$ represents a $C_1$–$C_4$ alkoxy or $C_1$–$C_4$ alkoxy-$C_2$–$C_4$ alkoxy substituted or unsubstituted aliphatic hydrocarbon radical containing from 1 to 18, more particularly from 1 to 4, carbon atoms of the type obtained by removing the hydroxyl group from a monohydric, unsubstituted primary or secondary aliphatic alcohol, or a cyclohexyl or 2-phenyl ethyl radical, and
n represents 1 or 2.

DETAILED DESCRIPTION OF THE PREFERRED EMBODIMENTS

The present invention is a process for producing urethanes in which urea and/or polyurets, primary amines, alcohols, N-unsubstituted urethanes and/or N-mono- or N,N'-disubstituted urethanes are reacted at a temperature of 120° to 350° C.

Starting materials for the process according to the present invention include urea or polyurets, particularly biuret, triuret or tetrauret, corresponding to the following general formula:

$$H_2N-(CO-NH)_m-H$$

wherein m represents an integer of from 1 to 4, or mixtures of these compounds.

Primary amines which may be used as a starting material in the present invention correspond to the general formula:

$$R_1(NH_2)_n$$

wherein $R_1$ and n are as defined above.

Examples of suitable amines include: methylamine; ethylamine; propylamine; isopropylamine; butylamine; i-butylamine; t-butylamine; hexylamine; dodecylamine; 2-ethyl-hexylamine; tetradecylamine; hexadecylamine;

octadecylamine; allylamine; 1,4-diaminobutane; 1,6-diaminohexane; 2,5-dimethyl-2,5-hexane diamine; trimethyl hexamethylene diamine; 2-methoxy-ethylamine; 3ethoxy-propylamine; 3-butoxy-propylamine; 1,4-butane diol-bis-(3-aminopropyl ether); 3-aminopropanoic acid-2-methyl propyl ester; 6-aminohexanitrile; lysine ester; 1,1-amino-undecanoic acid ester; cyclohexylamine; trimethyl cyclohexylamine; 2-norbornyl-methylamine; aniline; o-, m-, p-chloroaniline; 2,3-, 2,4-, 2,5-, 2,6-dichloroaniline; 3,4-dichloroaniline; p-, o-nitroaniline; m-, o-, p-tolylamine; 3-trifluoromethylaniline; 3-chloro-4-methylaniline; benzylamine; phenyl-cyclohexylamine; naphthylamine; 1,4-diaminocyclohexane; 2,4-, 2,6-diamino-1-methyl cyclohexane; 5-amino-1-aminomethyl-1,3,3-trimethyl cyclohexane; 4,4'-diaminodicyclohexylmethane; 4,4'-diamino-3,3'-dimethyldicyclohexylmethane; 1,3-diaminobenzene; 1,4-diaminobenzene; 2-chloro-1,4-diaminobenzene; 2,4-diaminotoluene; 2,6-diaminotoluene (and mixtures with 2,4-); 2-(N-ethylamino)-4-aminotoluene; 1,3-diamino-2-methylbenzene; 1,3-bis-aminomethylbenzene; 1,3-bis-aminoethyl-4,6-dimethylbenzene; 1,3-diamino-2,6-(4,6)-diethyl-4-methylbenzene; 1,3-diamino-2,4,6-triisopropylbenzene; 1,5-diaminonaphthalene; 2,7-diaminonaphthalene; benzidine; 3,3'-dichlorobenzidine; 4,4'-diaminodiphenylmethane (and crude products); 3,3'-dichloro-4,4'-diaminodiphenylmethane; 2,2-bis-(4-aminophenyl)-propane; 1,1-bis-(4-amino phenyl)-cyclohexane; 1,1-bis-(4-amino-3-methyl phenyl)-cyclohexane; 4,4',4''-triaminotriphenylmethane; 4,4'-diaminodiphenylether; 4,4',4''-triaminotriphenyl thiophosphate; p-methoxyaniline; p-ethoxyaniline; 1-(4-chlorophenoxy)-4-aminobenzene; 2,4-diaminodiphenylether; m-aminobenzoic acid esters, p-aminobenzoic acid ester; 3,5-diamino-2-methyl diphenylmethane; 3,5-diamino-4-methyl diphenylmethane (and mixtures thereof); 3,5-diamino-4-methyl dicyclohexylmethane; 3,5-diamino-2-methyl dicyclohexylmethane (and mixtures); 3,5,4'-triamino-4-methyl diphenylmethane; 3,5,4'-triamino-2-methyl dipheylmethane; 3,5,2'-triamino-4-methyl diphenylmethane; 3,5,2'-triamino-2-methyl diphenylmethane (and mixtures); 3,5,4'-triamino-4-methyl dicyclohexylmethane; 3,5,4'-triamino-2-methyl dicyclohexylmethane; 3,5,2'triamino-4-methyl dicyclohexylmethane; 3,5,2'-triamino-2-methyl dicyclohexylmethane (and mixtures); dibenzofuran amine; 1-aziridine propane amine; 4-pyridine methane amine; 2-pyridine amine; 1-(3-amino phenyl)-3-methyl-5-pyrazolone; pyrimidine amine; N-amino-morpholine and 2-aminobenzthiazole.

Particularly preferred amines include: propylamine; isopropylamine; n-butylamine; sec.butylamine; t-butylamine; stearylamine; hexamethylene diamine; cyclohexylamine; 3,3,5-trimethyl-5-aminomethyl cyclohexylamine; 4,4'-diamino-dicyclohexylmethane; aniline; p-chloroaniline; 3,4-dichloroaniline; m-tolylamine; p-methoxy aniline; 2,4-diaminotoluene; 2,6-diaminotoluene; 4,4'-diaminodiphenylmethane; 2,4'-diaminodiphenylmethane or technical mixtures of the abovementioned diaminotoluenes and diaminodiphenylmethanes.

Alcohols which may be used in the process of the present invention correspond to the general formula:

$$R_2\text{—OH}$$

wherein $R_2$ is as defined above.

Examples of suitable alcohols include: methanol; ethanol; propanol; i-propanol; butanol; i-butanol; pentanol; i-pentanol; hexanol; i-hexanol; heptanol; i-heptanol; octanol; i-octanol; nonanol; i-nonanol; decanol; i-decanol; dodecanol; 2-ethyl hexanol; β-chloroethanol; 2-ethyl butanol; hexadecanol; octadecanol; fatty alcohol mixtures; 2-methoxy ethanol; 2-ethoxy ethanol; 2-propoxy ethanol; 2-butoxy ethanol; 2-(2-methoxy ethoxy)-ethanol; 2-(2-ethoxy ethoxy)-ethanol; 2-(2-butoxy ethoxy)-ethanol; cyclopentanol; cyclohexanol; methyl cyclohexanol (and mixtures); cyclohexamethanol; 3,3,5-trimethyl cyclohexanol; 4-t-butylcyclohexanol; 2-hydroxy decalin; borneol; i-borneol; 1-(2-hydroxy ethoxy)-4-nitrobenzene; benzyl alcohol; 2-phenyl ethanol; 2-(methoxy phenoxy)-ethanol (and mixtures); 1-phenyl ethanol; 3-phenyl-1-propanol and 4-methoxy benzyl alcohol.

Particularly preferred alcohols include: methanol, ethanol, n-propanol, i-propanol, n-butanol, i-butanol, cyclohexanol, n-hexanol, 2-ethyl hexanol β-phenyl ethanol, glycol monomethyl ether, glycol monobutyl ether or diglycol monomethyl ether.

An essential characteristic of the present invention is the use of compounds containing carbonyl groups. Suitable carbonyl compounds include: N-unsubstituted urethanes and/or N-mono- or N,N'-disubstituted ureas or polyureas. Appropriate N-unsubstituted urethanes, i.e. simple carbamates, correspond to the general formula:

$$R_3\text{—O—CO—NH}_2$$

wherein $R_3$ preferably has the same definition as $R_2$ given above, $R_3$ and $R_2$ may represent the same or different radicals but it is preferred that $R_2$ and $R_3$ be identical radicals. However, $R_3$ may also represent an optionally chlorine- or $C_1$–$C_4$ alkyl-substituted aromatic hydrocarbon radical containing a total of from 6 to 15 carbon atoms.

Typical examples of suitable N-unsubstituted urethanes include: methyl, ethyl, n-propyl, i-propyl, n-butyl, i-butyl, cyclohexyl or n-hexyl carbamate or the carbamates derived from the other alcohols exemplified above or even phenyl, 2-chlorophenyl, 3-chlorophenyl, 4-chlorophenyl, 2-methylphenyl, 4-methylphenyl, 4-n-butylphenol or 1-naphthyl carbamate.

The organic N-mono- or N,N'-disubstituted ureas useful in the present invention may contain urethane or primary amino terminal groups. Linear polyureas having a maximum molecular weight of 2000 (those having a maximum molecular weight of 700 are particularly preferred) may also be useful as starting materials. The urea, urethane or amino groups should be attached to one another through hydrocarbon radicals. The urea groups may be substituted by hydrocarbon radicals which preferably correspond to the hydrocarbon radical of the reactant amine used. It is also preferred that the terminal urethane groups present, if any, be substituted on the oxygen atom by hydrocarbon radicals which preferably correspond to the hydrocarbon radical of the reactant alcohol. Typical examples of suitable ureas or polyureas include: N-methyl urea; N-ethyl urea; N-(n-propyl)-urea; N-(isopropyl)-urea; N-(n-butyl)-urea; N-(isobutyl)-urea; N-cyclohexyl urea; N-benzyl urea; N,N'-dimethyl urea; N,N'-diethyl urea; N,N'-di-(n-butyl)-urea; N,N'-dicyclohexyl urea; N,N'-dibenzyl urea; N,N'-di-(m-tolyl)-urea; N-phenyl urea; N,N'-diphenyl urea; N,N'-dicarbamoyl-2,4-tolylene diamine; N,N'-dicarbomoyl isophorone diamine or compounds corresponding to the following general formulae: 

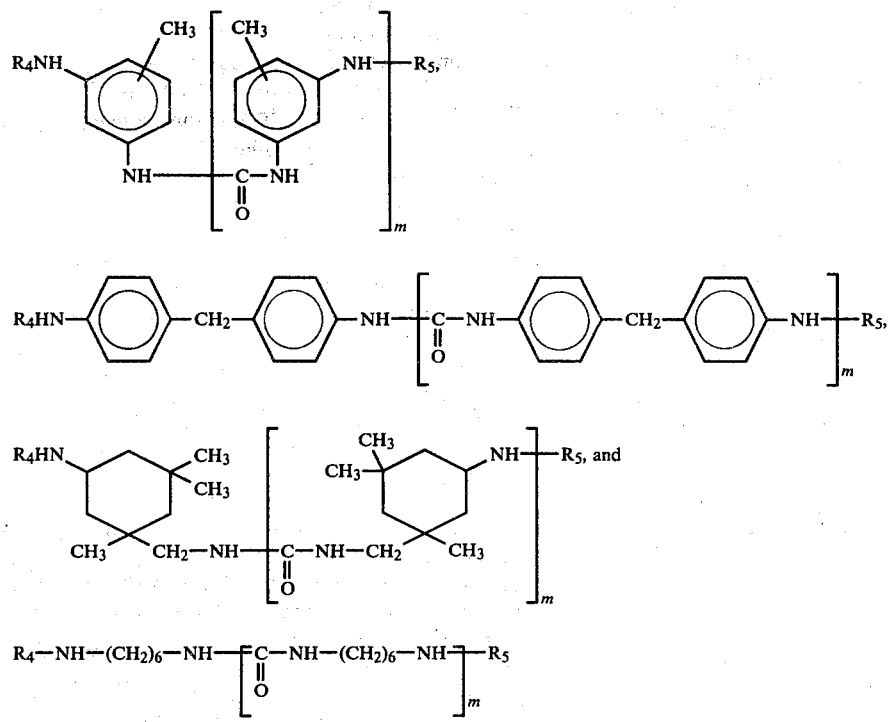

$$R_4\text{—NH—}(CH_2)_6\text{—NH}\underset{\phantom{O}}{\left[\overset{\phantom{O}}{\text{—C—NH—}(CH_2)_6\text{—NH—}}\right]_m}R_5$$
$$\phantom{R_4\text{—NH—}(CH_2)_6\text{—NH}}\overset{O}{\|}$$

wherein m represents a number of from 1 to 10,

R$_4$ and R$_5$ (which may be the same or different) each represent H, COOR$_2$, CONH$_2$ or CONHR$_6$, R$_6$ represents a monofunctional radical of the type described in the definition of R$_1$.

Other suitable ureas are, for example, the N,N'-disubstituted ureas or the corresponding polyureas which accumulate as secondary products in the processes described in U.S. Pat. Nos. 2,409,712 and 2,806,051. It is also possible to use substituted ureas synthesized by methods such as that described in D. F. Kutepow, Russ, Chem. Rev. 31, 633 (1962) or polyureas of the type described in H. Rinke, Houben-Weyl, XIV/2, 165 et seq.

In the process of the present invention, the reactant amine (including the amine chemically bound in the reactant N-mono- or N,N'-disubstituted urea where it corresponds to the reactant amine) is generally used in a quantity which is from 0.5 to 4 times the stoichiometric amount. Preferably, the amine is present in from 0.8 to 1.5 times the stoichiometric amount with 0.9 to 1.1 times the stoichiometric amount being the most preferred quantity. The alcohol (including the alcohol chemically bound in the N-unsubstituted and/or N-substituted ureas where it corresponds to the reactant alcohol component) is generally used in amounts from 1 to 10 times the stoichiometric amount with 1.1 to 4 times the stoichiometric quantity being the preferred quantity. The chemically bound alcohol content is based on the carbonyl groups present within urea, polyuret or urethane groups present in the reactant materials. The N-unsubstituted urea and/or the N-mono- or N,N'-disubstituted urea may each be used in a quantity of from 0 to 300% by weight, preferably from 0 to 150% by weight, based on the quantity of urea or polyurets. The total quantity of N-unsubstituted urea and N-mono- or N,N'-disubstituted urea should amount to at least 10% by weight, and preferably at least 30% by weight.

The process according to the present invention is preferably carried out in the presence of catalysts. Suitable catalysts include compounds which have a catalytic effect on the esterification of carboxylic acids. Particularly suitable catalysts are (i) inorganic or organic bases which are inert under the reaction conditions, (ii) Lewis acids, and (iii) salts and complex compounds (such as chelates) of transition materials.

Examples of suitable catalysts include: (a) tertiary amines such as tri-n-propylamine, triethylamine, triisopentylamine, diethyl benzylamine, N,N-dimethyl benzylamine, hexahydrodimethyl aniline, N-ethyl piperazine, diethyl-(2-methoxy propyl)-amine, ethoxy morpholine, N-(2-diethyl aminoethyl)-benzamide, N-(2-diethyl aminoethyl)-propionamide, 1,4-diaza-(2,2,2)-bicyclooctane, N,N-dimethyl-4-amino pyridine, 1-azabicycloheptanes, 1-azabicyclooctanes; (b) saturated polyheterocyclic amines such as 3-methyl conidine, 1-azabicyclo-(3,2,1)-octane, pyrrolizidines and quinuclidines; (c) inorganic bases such as beryllium hydroxide and sodium, potassium, lithium, magnesium, barium or calcium hydroxide; (d) basic alkali metal salts such as sodium carbonate, sodium sulfide, potassium carbonate and trisodium phosphate; and (e) alkali metal salts of fatty acids or sulfonic acids.

Suitable catalysts (ii) include Lewis acids such as iron(II) chloride, iron(III) chloride, zinc chloride, tin-(II) chloride, tin(IV) chloride, aluminum chloride, zinc cyanide, boron trifluoride and boron trifluoride etherate.

Suitable catalysts (iii) include (a) salts of transition metals (other than those which are Lewis acids) and (b) complex compounds (particularly chelates) of these metals. Suitable complex compounds include cobalt, manganese and lead naphthenates; iron oleates or carbonyls; acetylacetonates or iron, nickel, cobalt, zinc, lead, aluminum, manganese, magnesium, molybdenum, titanium, thorium, zirconium and vanadium; bis-(dibenzoyl methane)-copper; bis-(ethyl acetoacetate) of copper or iron; coordination compounds of titanium, zirconium, hafnium, thorium and manganese with $\beta$-diketones, $\beta$-ketoesters and $\beta$-hydroxy aldehydes; dibutyl tin dilaurate; dibutyl tin diacetate; di-(2-ethyl hexyl)-tin oxide; dioctyl tin oxide; zinc or tin salts of $C_1$–$C_{20}$ carboxylic acids such as zinc or tin(II) naphthanate, hexoate, calmitate, stearate or dimethyl valerate; acetates, chlorides, sulfates and octoates of divalent or trivalent cobalt; monovalent or divalent copper or divalent lead.

Particularly suitable catalysts include: zinc chloride, zinc acetate, zinc octoate, zinc oxide, zinc cyanide, tin(II) chloride, tin(IV) chloride, dibutyl tin dilaurate, cobalt triacetate, cobalt trichloride, cobalt trioctoate, copper(II) acetate, copper(I) chloride, copper(II) sulfate, lead acetate or lead chloride. The catalyst is generally used in a quantity of from 1 ppm to 20% by weight and preferably from 100 ppm to 5% by weight, based on the sum of the starting materials. In practice, every effort should, of course, be made to keep the catalyst concentration as low as possible. The optimal concentration will necessarily be dependent upon the type of starting materials used and the activity of the particular catalyst. The optimal catalyst concentration may, however, be readily determined by the techniques known to those in the art.

The process according to the present invention may be carried out under pressure or in the absence of applied pressure. The application of pressures of from 1 to 80 bars is, however, often appropriate if the reaction temperature is above the boiling point of one or more of the starting materials.

The process according to the present invention is generally carried out at temperatures of from 120° to 350° C., preferably from 130° to 300° C., and most preferably from 140° to 250° C.

The process according to the present invention may be carried out with or without solvents. Suitable solvents are solvents which are inert under the process conditions and which have a boiling point of from 100° to 280° C., preferably from 150° to 250° C. Examples of suitable solvents include: n-nonane; n-butyl cyclohexane; decahydronaphthalene; n-undecane; n-dodecane; n-hexyl cyclohexane; dipentene; 1-dodecane; isopropylbenzene; 1,3-diethylbenzene; indene; n-butylbenzene; tetralin; chlorobenzene; 4-chlorotoluene; 1,2-dichlorobenzene; 2,4-dichlorotoluene; 1,2,4-trichlorobenzene; 2-chloro-4-isopropyl-1-methylbenzene; anisole; cyclohexyl ethyl ether; diethylene glycol dimethyl ether; benzyl methyl ether; 4-methoxy toluene; parachloroanisole; di-n-hexyl ether; phenyl-n-propyl ketone; benzophenone; acetophenone; formamide; N,N-dimethyl formamide; N,N-diethyl formamide; N-methyl formamide; dimethyl acetamide; N-methyl pyrrolidone; caprolactam; phenol substituted phenols; sulfolan; hexamethyl phosphoric acid triamide; dimethyl sulfoxide; ethylene glycol monomethyl ether acetate; di-n-propyl carbonate; cyclohexyl acetate; diisobutyl carbonate; diethylene glcyol monomethyl ether acetate; diisoamyl carbonate; 2-ethyl pyridine; N,N-dimethyl-2-methylaniline; N,N-dimethylaniline; N-methyl-N-ethylaniline; N,N-dimethyl-2-chloroaniline; N,N-diethylaniline; quinoline; nitrocyclohexane; nitrobenzene; 2-nitrotoluene; 2,4-dimethyl-1-nitrobenzene; acetonitrile; N-capronitrile; benzonitrile; tolunitrile; diphenylether; tetramethylurea and phenyl acetonitrile. It is particularly preferred to use polar solvents and mixtures thereof. $\epsilon$-caprolactam is a particularly suitable solvent.

In many cases, such as where a large excess of alcohol is used, there is no need to use a solvent. The preparation of monourethanes from monoamines is another example of a reaction in which a solvent is unnecessary.

Since the reaction according to the present invention is accompanied by the elimination of ammonia, provision for removal of the ammonia must be made even when the reaction is carried out under pressure. Suitable measures for this removal include the installation of suitable excess-pressure valves in the reactor.

Where low-boiling alcohols are used, it is not essential that the reaction be carried out under pressure. The nonalcohol reactants may be heated to the reaction temperature and then added to the low-boiling alcohol at a rate such that the reaction temperature is maintained approximately constant.

To carry out the process according to the present invention, the reactants are preferably mixed and heated to the required reaction temperature. Where the reactant alcohol has a higher boiling point than the chemically bound alcohol component of the other reactants, the chemically bound alcohol components are generally removed in the course of the reaction so that the end product contains only the higher boiling alcohol component of the reactant alcohol. Where aromatic N-unsubstituted urethanes are used, there is no need to remove the hydroxyl component of the urethane by distillation.

It is also possible to carry out the process of the present invention by initially heating the reactants (with the exception of the primary amine) to the required reaction temperature while simultaneously displacing the chemically bound alcohols. The high-boiling, chemically bound alcohol of the N-unsubstituted urethanes and/or N-mono- or N,N'-disubstituted urea may be removed by distillation before the primary amine is added to the reaction mixture.

Ideally, all of the starting materials are incorporated into the end product of the process of the present invention. The following equations exemplify reactions which are typical of the process of the present invention:

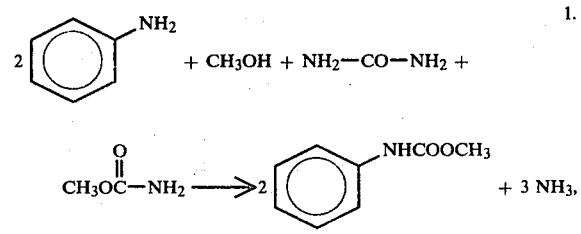

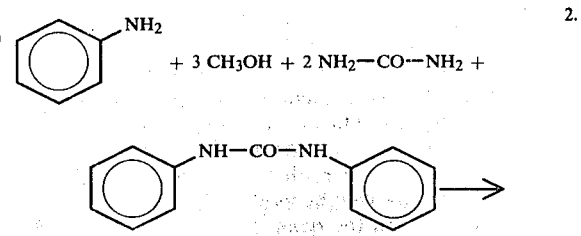

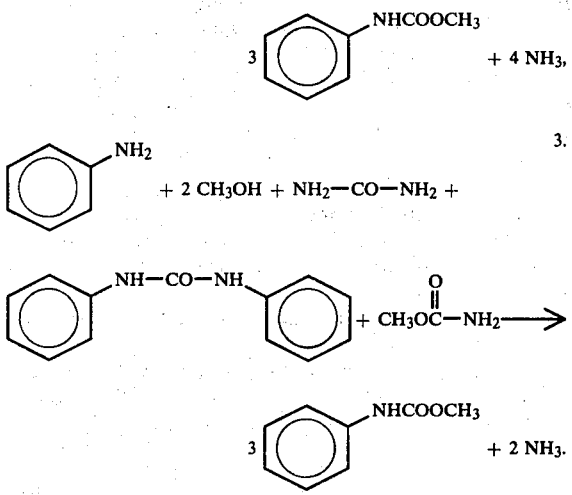

In practice, however, the end product will generally contain small quantities of the N-unsubstituted urea and/or N-mono- or N,N'-disubstituted urea. These incompletely reacted starting materials may be separated from the end product and reused.

The reaction time of the present invention is generally 2 to 15 hours, preferably 2 to 12 hours. The reaction mixture may be worked up in any manner known to those in the art such as distilling off volatile materials. It is particularly desirable that such distillation be carried out after insoluble constituents such as insoluble catalysts have been filtered off. In cases where the reaction mixture is worked up by distillation, the product urethane generally accumulates as the final fraction collected or as the distillation residue. Any of the reactant substituted urea present in the end product may be separated by techniques known to those in the art. One such separation technique is taking up the distillation residue in a suitable selective solvent (e.g., white spirit) and subsequently filtering off the unreacted urea starting material.

The process according to the present invention yields a N,O-disubstituted urethane in quantities which are substantially larger than those of prior art processes. The fact that this result is achieved by using N-unsubstituted ureas and/or N-mono- or N'-disubstituted ureas is particularly surprising because U.S. Pat. Nos. 2,409,712 and 2,806,051 teach that these same components are undesirable secondary products which are responsible for a comparatively poor yield.

The products obtained by the process according to the present invention represent valuable starting materials for preparing the isocyanates on which they are based. Preparation of organic isocyanates from the urethanes of the present invention is carried out by thermally splitting the urethanes into the isocyanate and the alcohol on which they are based by techniques known to those in the art. There is generally no need for the products of the present invention to be purified before they are split into an isocyanate and an alcohol.

Having thus described our invention, the following Examples are given by way of illustration. The percentages given in these Examples represent percentages by weight unless otherwise specified.

EXAMPLES

Example 1

A pressure apparatus was used as a reaction vessel where the product urethane had a low-boiling point. The pressure vessel used was made of steel, had a capacity of 5 liters and could withstand pressures up to 64 bars. The reactor vessel was equipped with a stirrer, a jacket heating system and a packed column (steel, nominal width, 50 mm). The pressure vessel served as both a reaction vessel and a sump vessel for the column. The column was packed with rings of steel wire mesh cloth (4 mm) to a level of approximately 1 meter. The column was also provided with a coil condenser (as the head condenser) above which there was a valve for removing gases.

931 g of aniline, 360 g of urea, 356 g of ethyl carbamate, 1160 g of ethanol (approximately 96%) and 5.3 g of zinc octoate were introduced into the pressure vessel. After the pressure vessel and the column had been purged with nitrogen, the mixture was heated while being stirred. By adjusting the head condenser and the valve at the head of the column, the pressure prevailing in the apparatus was regulated in such a way that it was just sufficient to achieve the required reaction temperature. The mixture was heated to 200° C. and maintained at 200° C. for 6.0 hours. The ammonia given off was rectified in the column and thus separated from covolatilizing substances. The ammonia gas removed was substantially pure. On completion of the reaction, the mixture was cooled and the apparatus vented. The reaction mixture was removed from the pressure vessel, filtered and subjected to fractional distillation. Most of the excess alcohol was initially separated off at atmospheric pressure. The mixture was then distilled at 0.2 mbar. 1435 g (96.9% of the theoretical yield) of N-phenyl carbamic acid ethyl ester having a melting point of from 50° to 51° C. were obtained.

EXAMPLE 2

Following the procedure described in Example 1, 745 g of aniline, 255 g of N,N'-diphenyl urea, 481 g of urea, 1333 g of methanol and 6.0 g of zinc octoate were reacted for 3.5 hours at 200° C. in the pressure apparatus described in Example 1. The mixture was then cooled and, after the apparatus had been vented, another 72 g of urea were added. The mixture was then reheated and reacted for 4 hours at 200° C. After cooling and venting of the apparatus, the mixture was removed, filtered and subjected to fractional distillation. Most of the methanol excess was separated off at atmospheric pressure. The product was then distilled at 0.2 mbar. 1323 g (84.1% of the theoretical yield) of N-phenyl carbamic acid methyl ester melting at from 45° to 47° C. were obtained.

Example 3

Following the procedure of Example 1, 745 g of aniline, 849 g of N,N'-diphenyl urea, 480 g of urea, 356 g of ethyl carbamate and 1350 g of ethanol (approximately 96%) were reacted for 5.5 hours at 200° C. in the pressure apparatus described in Example 1. After cooling and venting of the apparatus, the reaction mixture was removed, filtered and subjected to fractional distillation. After the excess alcohol had been separated (at normal pressure), the remaining fraction was subjected to distillation at 0.2 mbar. 1934 g (73.2% of the theoretical yield) of N-phenyl carbamic acid ethyl ester melting at from 49° to 51° C. were produced.

Example 4

Following the procedure described in Example 1, 638 g of 4-chloroaniline, 240 g of urea, 89 g of ethyl carbamate, 625 g of ethanol (approximately 96%) and 1400 g of chlorobenzene were reacted for 6.5 hours at 200° C. in the pressure apparatus described in Example 1. After the apparatus had been cooled and vented, the reaction mixture was removed. Excess ethanol was removed by fractional distillation at atmospheric pressure. The mixture (while being stirred) was then exposed to hydrogen chloride gas at room temperature, filtered and subjected to fractional distillation in vacuo. Chlorobenzene was separated off at 15 mbar. Subsequent distillation at 0.2 mbar yielded 785 g (78.6% of the theoretical yield) of N-(4-chlorophenyl)-carbamic acid ethyl ester melting at from 68° to 70° C.

Example 5

169 g of a polyurea mixture based on 2,4-diaminotoluene containing terminal aminotolyl groups (average molecular weight, 1500) were introduced into the apparatus described in Example 1. 428 g of 2,4-diaminotoluene, 384 g of urea, 168 g of ethyl carbamate, 1700 g of ethanol (approximately 96%) and 5.2 g of zinc octoate were then added. The mixture was reacted for 6.0 hours at 200° C. in the same way as in Example 1. After cooling and venting of the apparatus, the reaction mixture was removed, filtered and analyzed by high pressure liquid chromatography. A yield of 937 g (75% of the theoretical yield) of 2,4-bis-(ethoxy carbonyl amino)-toluene was determined.

Example 6

Following the procedure described in Example 1, 611 g of 2,4-diaminotoluene, 480 g of urea, 178 g of ethyl carbamate and 1590 g of ethanol (approximately 96%) were reacted for 6.5 hours at 200° C. in the pressure apparatus described in Example 1. After cooling and venting of the apparatus, the reaction mixture was removed, filtered and analyzed by liquid chromatography (HPLC). A yield of 881 g (66% of the theoretical yield) of 2,4-bis-(ethoxy carbonyl amino)-toluene was determined.

Example 7

Following the procedure described in Example 1, 892 g of 4,4'-diaminodiphenylmethane, 432 g of urea, 186 g of isopropyl carbamate and 151 g of isopropanol were reacted for 7.0 hours at 200° C. in the described pressure apparatus. After cooling and venting of the apparatus, the reaction mixture was removed and filtered. The voluminous filter residue was repeatedly extracted with boiling isopropanol and the combined solutions were then analyzed by liquid chromatography (HPLC). A yield of 1080 g (65% of the theoretical yield) of 4,4'-bis-(isopropoxy carbonyl amino)-diphenylmethane was determined.

Example 8

520 g (4 mols) of 2-ethyl hexanol, 128 g (0.5 mols) of N,N'-dicarbamoyl isophorane diamine and 0.9 g of zinc octoate were heated under reflux for 3 hours and, after cooling to 110° C., 60 g (1 mol) of urea and 85 g (0.5 mol) of isophorone diamine were added. The mixture was then heated under reflux for another 12 hours. Excess 2-ethyl hexanol was distilled off at a sump temperature of 120° C./0.1 Torr, leaving 433 g of residue. This residue hardened to form a glass-like mass which, according to IR and NMR analysis, was 85% of 1-[(2-ethyl hexoxy)-carbonyl amino]-3,3,5-trimethyl-5-[(2-ethyl hexoxy)-carbonyl amino methyl]-cyclohexane. This yield was 76% of the theoretical yield.

Example 9

102.3 g (1.1 mol) of aniline, 300 g (3 mols) of cyclohexanol, 60 g (1 mol) of urea, 136.2 g (1 mol) of phenyl urea and 3 g of cobalt naphthanate were heated under reflux for 3 hours. After the sump temperature had reached 200° C., the mixture was maintained at that temperature for another 4 hours.

The yield of O-cyclohexyl-N-phenyl urethane was determined by high pressure liquid chromatography (HPLC) to be 93% of the theoretical yield.

Example 10

109 g (1.1 mol) of cyclohexylamine, 90 g (1.5 mols) of urea, 366 g (3 mols) of β-phenyl ethanol and 112 g (0.5 mol) of N,N'-dicyclohexyl urea were heated for 10 hours at 200° C. The fraction which was insoluble in ethyl acetate was separated off. 439 g N-cyclohexyl-O-β-phenyl ethyl urethane corresponding to 89% of the theoretical yield, melting at 93° C. (cleaning spirit) were isolated.

Example 11

102.3 g (1.1 mols) of aniline, 300 g (3 mols) of cyclohexanol, 51.5 g (0.5 mol) of biuret and 136.2 g of phenyl urea were heated under reflux for 16 hours. The yield of O-cyclohexyl-N-phenyl urethane was determined by high pressure liquid chromatography to be 71% of the theoretical yield.

Example 11a

The reaction of Example 11 was repeated using 0.7 g of zinc octoate. The reaction mixture was heated under reflux for 9 hours. The yield of O-cyclohexyl-N-phenyl urethane was determined by high pressure liquid chromatography to be 96% of the theoretical yield.

Example 12

204.6 g (2.2 mols) of aniline, 300 g (3 mols) of cyclohexanol, 96 g (1.6 mols) of urea and 54.4 g (0.4 mol) of carbamic acid phenyl ester were heated under reflux to 200° C. with 1 g of triethylenediamine. The mixture was maintained at that temperature for 7 hours. The yield of O-cyclohexyl-N-phenyl urethane was determined by high pressure liquid chromatography to be 87% of the theoretical yield.

Example 13

93 g (1 mol) of aniline, 90 g (1.5 mols) of urea, 106 g (0.5 mol) of N,N'-diphenyl urea and 427 g (3.5 mols) of β-phenyl ethanol were heated for 2 hours to 200° C. After another 7 hours at 200° C., a yield of 88% of the theoretical yield of N-phenyl-O-β-phenyl ethyl urethane was determined by high pressure liquid chromatography.

Example 14

139.5 g (1.5 mols) of aniline, 244 g (2 mols) of β-phenyl ethanol, 60 g (1 mol) of urea and 44.5 g (0.5 mol) of carbamic acid ethyl ester were heated under reflux with 0.8 g of zinc octoate. The ethanol formed was distilled off. After 2.5 hours, the temperature reached 200° C. and was maintained at that level for another 9 hours. Analysis by high pressure liquid chromatography indicated that N-phenyl-O-β-phenyl ethyl urethane had formed in an amount which was 89% of the theoretical yield.

Example 15

6 ml of zinc octoate were added to 212 g of N,N'-diphenyl urea (1 mol), 75 g of carbamic acid methyl ester (1 mol), 93 g of aniline (1 mol), 60 g of urea (1 mol) and 400 g of cyclohexanol (4 mols). The mixture was then heated for 3 hours to 200° C. The methanol formed was distilled off during the reaction. The mixture was maintained at 200° C. for another 4 hours, after which 90 g of cyclohexanol were distilled off in a water jet vacuum. 96.5% of the residue (665 g) was N-phenyl-O-cyclohexyl urethane (as determined by HPLC). The product urethane had a melting point of 81°-82° C. (from cleaning spirit).

Example 16

3 ml of zinc octoate were added to 93 g of aniline (1 mol), 60 g of urea (1 mol), 212 g of N,N'-diphenyl urea (1 mol), 143 g of cyclohexyl carbamate (1 mol) and 270 g of cyclohexanol (2.7 mols) and the mixture heated to 150° C. The internal temperature rose to 190° C. in 4 hours. The reaction mixture was then stirred at 200° C. for 5 hours. On completion of the reaction, the cyclohexanol still present was distilled off in a water jet vacuum. 96% of the residue (660 g) was N-phenyl-O-cyclohexyl urethane (as determined by HPLC). The product urethane had a melting point of 81°-82° C. (from cleaning spirit).

Example 17

240 g of 3,3'-dimethyl-N,N'-diphenyl urea (1 mol), 107 g of 3-aminotoluene (1 mol), 120 g of urea (2 mols) and 488 g of 2-phenyl ethanol (4 mols) were mixed. Two grams of aluminum chloride were then added and the resultant mixture was then rapidly heated until the elimination of $NH_3$ began. The temperature was then increased to 200° C. over a period of 2 hours and maintained at that level for 6 hours. Unreacted 2-phenyl ethanol was then distilled off in an oil pump vacuum. 628 g of N-(m-tolyl-O-(2-phenyl ethyl)-urethane (82% of the theoretical yield) having a melting point of 52°-53° C. (from petroleum ether) were obtained.

Example 18

200 ml of zinc octoate were added to 9.3 kg of aniline (100 mols), 6 kg of urea (100 mols), 21.2 kg of N,N'-diphenyl urea (100 mols), 14.3 kg of cyclohexyl carbamate (100 mols) and 26 kg of cyclohexanol (260 mols). The resulting mixture was then heated to 155° C. The internal temperature rose to 190° C. in 5 hours and then to 200° C. over a period of another hour. The reaction mixture was then stirred at 200° C. for 5 hours. On completion of the reaction, excess cyclohexanol was distilled off in a water jet vacuum. HPLC indicated that 95% of the residue was N-phenyl cyclohexyl urethane.

260 g of cyclohexyl carbamate were removed from the reaction residue by vacuum distillation. The thus-obtained residue was taken up in 100 liters of hot washing spirit and subsequently filtered. 638 g of diphenyl urea remained on the filter after drying. The spirit solution used as a wash was concentrated and an N-phenyl cyclourethane substantially free of secondary products was thus obtained. 61.76 kg of N-phenyl-O-cyclohexyl urethane (94% of the theoretical yield) having a melting point of 81°-82° C. (from cleaning spirit) were recovered.

Example 18a 14.04 kg of cyclohexyl carbamate and 260 g of cyclohexyl carbamate (recovered from the process of Example 18) were used rather than 14.3 kg of pure cyclohexyl carbamate (100 mols). The procedure was the same as that described in Example 18. 61.8 kg of N-phenyl-N-cyclohexyl urethane (94% of the theoretical yield) were produced.

Example 18b

The procedure of Example 18 was repeated using 20.6 kg of fresh N,N'-diphenyl urea together with 600 g of N,N'-diphenyl urea recovered from the process of Example 18a. 61.78 kg of N-phenyl-O-cyclohexyl urethane (94% of the theoretical yield) having a melting point of 81°-82° C. (from cleaning spirit) were collected.

Example 18c

The procedure of Example 18 was repeated using 1.2 kg of N,N'-diphenyl urea and 500 g of cyclohexyl carbamate recovered from the processes of Examples 18, 18a and 18b. The quantities of pure N,N'-diphenyl urea and pure cyclohexyl carbamate used in Example 18 were reduced by the amount of the previously recovered materials used. 61.85 kg of N-phenyl-O-cyclohexyl urethane (95% of the theoretical yield) having a melting point of 82° C. (from cleaning spirit) were recovered.

Example 19

103.2 g (0.6 mol) of N,N-diisobutyl urea, 351 g (3 mols) of carbamic acid butyl ester, 60 g (1 mol) of urea and 10 g of dibutyl tin oxide were introduced into a 1-liter, 4-necked flask equipped with a stirrer, reflux condenser, contact thermometer and dropping funnel. This mixture was heated to 120° C. 247 g (3.4 mols) isobutylamine were then added dropwise with further heating to 180° C. 3 mols of ammonia were given off and collected in dilute sulfuric acid. 185 g (2.5 mols) of n-butanol were then added dropwise over a period of another 4 hours in such a way that the temperature of 180° C. was maintained under continuous reflux. Thereafter, the amount of ammonia given off amounted to 4.6 mols (92% of the theoretical amount).

The mixture was then subjected to fractional distillation. After a first fraction of 120 g of n-butanol and a second fraction of 40 g of carbamic acid-n-butyl ester, N-isobutyl-O-(n-butyl)-urethane (Bp, 14 mm: 114° C.) was obtained in a yield of 676 g (3.9 mols=85% of the theoretical yield).

Example 20

300 g of benzyl naphthalene (isomer mixture) as solvent, 428 g (4 mols) of m-toluidine, 103 kg (1 mol) of carbamic acid isopropyl ester, 240 g (4 mols) of urea, 242 g (1 mol) of di-m-tolyl urea and 10 g of zinc dioctoate were heated in a 2-liter, 4-necked flask equipped with a stirrer, contact thermometer, reflux condenser and dropping funnel. The elimination of ammonia began at 130° C. The ammonia gas was absorbed in dilute sulfuric acid for the purpose of monitoring the reaction. 300 g (5 mols) of isopropanol were added dropwise under continuous reflux over a period of 5 hours in such a way that the sump temperature gradually rose to 180° C. During this period, 6.5 mols of ammonia were given off. The mixture was then maintained at 180° C. for 3 hours, during which time the reflux was maintained by the continuous dropwise addition of isopropanol. The total quantity of ammonia eliminated was 8.5 mols (94% of the theoretical yield).

The mixture was then subjected to fractional distillation. After a first fraction of isopropanol, carbamic acid isopropyl ester and m-toluidine, N-(m-tolyl)-O-isopropyl urethane was distilled over at 124° C./14 mm. The urethane was separated from codistilled di-m-tolyl urea by filtration. 857 g (74% of the theoretical yield) of the product urethane were collected.

EXAMPLE 21

97.6 g (0.8 moles) of 2,4-diaminotoluene, 24.4 g (0.2 moles) of 2,6-diaminotoluene, 114 g (0.9 moles) of urea, 37.5 g (0.5 moles) of carbamic acid methyl ester, 250 g (2.5 moles) of cyclohexanol and 0.3 g of zinc octoate are heated to reflux temperature while methanol which is being formed is continuously distilled off. Cyclohexanol is added simultaneously at such a rate that the temperature of the reaction mixture is maintained at 180° C. Within 18 hours 2,4- and 2,6- bis-(cyclohexoxy-carbonyl-amino-) toluene is formed in an amount which corresponds to 94% of the theoretical yield (HPLC analysis).

Example 22

120 g (2 moles) of urea, 480 g (4 moles) of diethylene glycol monomethylester, 35.6 g (0.4 moles) of carbamic acid ethyl ester and 2 g of zinc octoate are heated to reflux temperature for one hour while ethanol which is being formed is continuously distilled off. Subsequently 198 g (1 mole) of 4,4'-diaminodiphenylmethane is added dropwise within a period of time of two hours while the temperature of the reaction mixture is maintained at a reflux temperature of 200° C. by the simultaneous addition of diethylene glycol dimethylether. After a total reaction time of 7 hours 4,4'-bis-[2-(2-methoxyethoxy-)ethoxycarbonylamino]-diphenylmethane is formed in an amount which corresponds to 93.5% of the theoretical yield (HPLC analysis).

Example 23

A 0.5 l reaction vessel is equipped with a stirrer, dropping thunnel and a reflux condenser with a gas outlet tube. The inlet tube of the dropping thunnel immerses into the reaction mixture and is rinsed with nitrogen. 60.1 g of urea, 93.1 g of aniline, 21.2 g of N,N'-diphenylurea and 0.5 g of dibutyl-tin-dioxide are heated under stirring to 170° C. within 30 minutes while nitrogen is continuously introduced into the reaction vessel. Subsequently 73 g of ethanol are dropped into the reaction mixture within 10 minutes so that the temperature of the reaction mixture is maintained at 170°–175° C. After 10 hours the reaction is stopped by cooling to room temperature. 156.5 g (86% of the theoretical yield) of N-phenyl-carbamic acid ethyl ester are formed according to HPLC analysis.

Example 24

Following the procedure of example 23 60.1 g of urea, 93.1 g of aniline, 8.9 g of ethyl carbamate and 0.5 g of dibutyl-tin-oxide are heated to 170° C. Subsequently 84 g of ethanol are added dropwise at such a rate that the reaction temperature can be maintained between 170° and 175° C. After a total reaction time of 10 hours the reaction is stopped by cooling to room temperature. 161 g (98% of the theoretical yield) of N-phenyl-carbamic acid ethyl ester are found by HPLC analysis.

What is claimed is:

1. A process for the preparation of N,O-disubstituted urethanes by reacting
   (a) urea or polyurets with
   (b) primary amines and
   (c) alcohols
at temperatures of from 120° to 350° C. in which N-mono- or N,N'-disubstituted ureas or polyureas are also used as reactants.

2. The process of claim 1, wherein the reaction is carried out in the presence of esterification catalysts for carboxylic acids.

3. The process of claim 1, wherein the reaction is carried out in the presence of polar solvents.

4. The process of claim 3, wherein the solvent is ε-caprolactam.

5. The process of claim 1, wherein the N-mono- or N,N'-disubstituted ureas or polyureas are present in an amount which is at least 10% by weight of the total reactants used.

6. The process of claim 1, wherein the N-mono- or N,N'-disubstituted ureas or polyureas are present in an amount which is at least 30% by weight of the total reactants used.

7. The process of claim 1, wherein a N-unsubstituted urethane is present in an amount of 0–150% by weight, based upon the quantity of component (a).

8. The process of claim 1, wherein the N-mono- or N,N'-disubstituted ureas or polyureas are present in an amount of 0 to 150% by weight, based upon the quantity of component (a).

9. The process of claim 1, wherein the N-mono- or N,N'-disubstituted ureas or polyureas have a chemically bound amine corresponding to component (b).

10. The process of claim 1, wherein the N-mono- or N,N'-disubstituted ureas or polyureas have a chemically bound alcohol which corresponds to component (c).

11. A process for the preparation of N,O-disubstituted urethanes by reacting
    (a) urea or polyurets with
    (b) aliphatic primary amines and
    (c) alcohols
at temperatures of from 120° to 350° C., characterized in that
    (d) N-unsubstituted urethanes and/or
    (e) N-mono- or N,N'-disubstituted ureas or polyureas are also used as reactants.

12. The process of claim 11 wherein components (d) and (e) are present in an amount which is at least 10% by weight of the total reactants used.

13. The process of claim 11 wherein components (d) and (e) are present in an amount which is at least 30% by weight of the total reactants used.

14. The process of claim 11 wherein component (d) is present in an amount of 0–150% by weight, based upon the quantity of component (a).

15. The process of claim 11 wherein component (e) is present in an amount of 0–150% by weight, based upon the quantity of component (a).

* * * * *